United States Patent
Burnes et al.

(10) Patent No.: US 8,676,310 B2
(45) Date of Patent: Mar. 18, 2014

(54) IMPLANTABLE MEDICAL DEVICE INCLUDING TWO POWER SOURCES

(75) Inventors: John E. Burnes, Coon Rapids, MN (US); Paul G. Krause, Shoreview, MN (US); William T. Donofrio, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 1174 days.

(21) Appl. No.: 12/609,637

(22) Filed: Oct. 30, 2009

(65) Prior Publication Data

US 2010/0114215 A1 May 6, 2010

Related U.S. Application Data

(60) Provisional application No. 61/110,393, filed on Oct. 31, 2008.

(51) Int. Cl.
*A61N 1/00* (2006.01)
*A61B 5/04* (2006.01)

(52) U.S. Cl.
USPC ....... 607/5; 607/6; 607/34; 607/119; 600/373

(58) Field of Classification Search
USPC ............................. 607/5–6, 34, 119; 600/373
See application file for complete search history.

(56) References Cited

U.S. PATENT DOCUMENTS

| | | | |
|---|---|---|---|
| 4,096,866 A | 6/1978 | Fischell | |
| 4,590,941 A | 5/1986 | Saulson et al. | |
| 5,199,428 A | 4/1993 | Obel et al. | |
| 5,203,326 A | 4/1993 | Collins | |
| 5,218,960 A | 6/1993 | Privas | |
| 5,235,979 A | 8/1993 | Adams | |
| 6,008,625 A | 12/1999 | Gan et al. | |
| 6,744,152 B2 | 6/2004 | Kroll | |
| 6,833,983 B2 | 12/2004 | Nguyen et al. | |
| 6,871,090 B1 | 3/2005 | He et al. | |
| RE38,777 E | 8/2005 | Adams et al. | |
| 7,136,701 B2 | 11/2006 | Greatbatch et al. | |
| 7,191,008 B2 | 3/2007 | Schmidt et al. | |
| 7,269,457 B2 | 9/2007 | Shafer et al. | |
| 7,587,238 B2 | 9/2009 | Moffitt et al. | |
| 2001/0002441 A1 | 5/2001 | Boveja | |
| 2004/0030366 A1 | 2/2004 | Kurashurov | |
| 2004/0147972 A1* | 7/2004 | Greatbatch et al. | 607/34 |
| 2004/0220626 A1* | 11/2004 | Wagner | 607/4 |

(Continued)

FOREIGN PATENT DOCUMENTS

RU 2336104 C1 10/2008

*Primary Examiner* — Nicole F Lavert
(74) *Attorney, Agent, or Firm* — Reed A. Duthler

(57) ABSTRACT

An implantable medical device (IMD) may include a battery dedicated to providing cardiac stimulation therapy and a separate power source that provides power for electrical stimulation therapy. Such a configuration preserves the battery dedicated for providing cardiac stimulation therapy even if the second power source is depleted. As an example, the IMD may comprise a cardiac stimulation module configured to deliver at least one stimulation therapy selected from a group consisting of pacing, cardioversion and defibrillation. The IMD further comprises a electrical stimulation module configured to deliver electrical stimulation therapy, a first power source including a battery, wherein the first power source is configured to supply power to the cardiac stimulation module and not to the electrical stimulation module, and a second power source. The second power source is configured to supply power to at least the electrical stimulation module.

23 Claims, 5 Drawing Sheets

(56) References Cited

U.S. PATENT DOCUMENTS

2006/0136007 A1 6/2006 Mickle et al.
2007/0142872 A1 6/2007 Mickle et al.
2007/0156179 A1 7/2007 S.E.
2009/0036943 A1 2/2009 Signoff et al.
2009/0216292 A1 8/2009 Pless et al.

* cited by examiner

IMPLANTABLE MEDICAL DEVICE INCLUDING TWO POWER SOURCES

CROSS-REFERENCE TO RELATED APPLICATIONS

This application claims the benefit of U.S. Provisional Application No. 61/110,393, filed on Oct. 31, 2008. The disclosure of the above application is incorporated herein by reference.

TECHNICAL FIELD

The disclosure relates to implantable medical devices, and, more particularly, to implantable medical devices for delivering stimulation therapy.

BACKGROUND

A wide variety of implantable medical devices (IMDs) that deliver a therapy or monitor a physiologic condition of a patient have been clinically implanted or proposed for clinical implantation in patients. Some IMDs may employ one or more elongated electrical leads and/or sensors. Such IMDs may monitor or deliver therapy to the heart, muscles, nerves, the brain, the stomach or other organs. In some cases, IMDs deliver electrical stimulation therapy and/or monitor physiological signals via one or more electrodes or sensor elements, which may be included as part of one or more elongated implantable medical leads. Implantable medical leads may be configured to allow electrodes or sensors to be positioned at desired locations for delivery of stimulation or sensing electrical depolarizations. For example, electrodes or sensors may be located at a distal portion of the lead, and a proximal portion of the lead may be coupled to an IMD housing, which may contain electronic circuitry such as stimulation generation and/or sensing circuitry.

Implantable cardiac devices, such as cardiac pacemakers or implantable cardioverter defibrillators, provide therapeutic stimulation to the heart by delivering electrical therapy signals such as pulses or shocks for pacing, cardioversion or defibrillation via electrodes of one or more implantable leads. In some cases, an implantable cardiac device may sense intrinsic depolarizations of the heart, and control the delivery of therapeutic stimulation to the heart based on the sensing. When an abnormal rhythm of the heart is detected, such as bradycardia, tachycardia or fibrillation, an appropriate electrical therapy (e.g., in the form of pulses) may be delivered to restore the normal rhythm. For example, in some cases, an IMD may deliver pacing, cardioversion or defibrillation signals to the heart of the patient upon detecting ventricular tachycardia, and deliver cardioversion or defibrillation therapy to a patient's heart upon detecting ventricular fibrillation.

Some proposed medical device systems may include a neurostimulator in addition to the implantable cardiac device. As one example, a medical device system may include a spinal cord stimulator and an implantable cardioverter-defibrillator, whereby the spinal cord stimulator may deliver neurostimulation to reduce pain associated with delivery of defibrillation shocks or may provide neurostimulation to assist in regulation of heart rhythms. Examples of such devices include those described in U.S. Pat. No. 5,203,326, issued to Collins eta al., U.S. Pat. No. 5,792,187 issued to Adams, U.S. Pat. No. 5,562,689 issued to Ellsberry, et al. and U.S. Pat. No. 5,994,428 issued to Obel, et al., all of which are incorporated herein by reference in their entireties. Prior art medical devices employing multiple power sources are disclosed in U.S. Pat. No. 6,238,813 issused to Maile, et al., U.S. Pat. No. 5,235,979 issued to Adams and U.S. Pat. No. 4,437,466 issued to Stanley et al., all incorporated herein by reference in their entireties.

SUMMARY

As described herein, IMDs including both cardiac stimulation capability and neurostimulation capability may include more than one power source. The power sources may be batteries, capacitors or alternative power sources. In some embodiments as described below, the first source may be non-rechargeable and the second source may be rechargeable. In other embodiments both power sources may be rechargeable. Rechargeable power sources and associated power supply circuitry may, for example, correspond to those disclosed in U.S. Pat. No. 5,314,451 issued to Mulier, U.S. Pat. No. 4,119,103 issued to Jirak, U.S. Pat. No. 3,942,535 issued to Schulman, U.S. Pat. No. 7,167,756 issued to Torgerson, et al., U.S. Pat. No. 4,653,198 issued to Torgerson, et al., U.S. Pat. No. 4,996,886 issued to Fischell or U.S. Pat. No. 6,505,077 issued to Kast, et al., all incorporated herein by reference in their entireties.

In some embodiments, an IMD practicing the invention may include a first power source dedicated to providing cardiac stimulation therapy and a second power source that normally provides power for a second electrical stimulation therapy such as neurostimulation therapy. On depletion of the second source, the second stimulation therapy may be disabled while cardiac stimulation using the first source may be continued. Such a configuration preserves the battery dedicated for providing cardiac stimulation therapy even if the second power source is depleted. In this manner, the reliability of a cardiac stimulator can be maintained in an IMD configured to provide both cardiac stimulation and neurostimulation, muscle stimulation or the like. While the disclosed embodiment focuses on specific types of neurostimulation as the second stimulation therapy, the invention is believed applicable to a range of stimulation therapies including spinal cord stimulation, vagal nerve stimulation, baroreceptor stimulation, skeletal muscle stimulation and smooth muscle stimulation. The disclosed examples are in this sense exemplary and should not be taken as limiting the applicability of the invention.

In some embodiments otherwise as described above, provision may additionally be made to disable neurostimulation responsive to depletion of the first source accompanied by switching to the second source to power the cardiac stimulator until the device can be replaced.

By using one source as a power supply for cardiac stimulation and one source as a power supply for neurostimulation, the cardiac stimulation and power supply circuitry may be separate and isolated from the neurostimulation and power supply circuitry. The two power sources may thus also be isolated from each other. Benefits of isolating one source from the other include reduction of crosstalk and reduction of shunt current. The ability to isolate the power sources is particularly beneficial in the context of protecting the neurostimulation circuitry during delivery of high energy cardiac stimulation therapy such as cardioversion or defibrillation, which may otherwise induce unwanted signals in the neurostimulation circuitry. For purposes of the present disclosure, isolation of the power sources may be understood to preferably include isolation between of the outputs (V+) and the circuit grounds (G) of the power sources from one another. The components supplied by the isolated power sources may correspondingly also be isolated from one another in the same fashion. As discussed below, this isolation may be provided by means of switching circuitry or may in certain embodiments be made by means of separate hard-wired connections between the power sources and the circuitry components they supply.

In alternative embodiments, the second source may be used to normally power both cardiac and neurostimulation therapies. In these embodiments, responsive to depletion of the second source, neurostimulation may be disabled and cardiac stimulation thereafter powered by the first source.

In embodiments in which the second power source is a rechargeable power source, on an as-needed or scheduled basis there may also be a temporary connection of the two power sources two batteries via direct connect (parallel) or via a recharge circuit, such that the partially depleted rechargeable second power source is recharged by the more robust first power source. The temporary connection can be initiated upon detection of low voltage from the rechargeable second power source, upon detection of defined amount of charge removed from the rechargeable second power source or upon a predetermined schedule. During this temporary common connection time, certain functions that are adversely influenced by the common connection may be eliminated or modified. Recharge can be brief, but repetitive, such as on a portion of each cardiac cycle basis or for a period of time, such as seconds to minutes. The amount of charge energy provided by the more robust first power source can be limited, in order to avoid excessive depletion of the first power source. This arrangement is beneficial for patients that are not always responsible to or able to recharge their device. It provides some grace recharges they can call upon when necessary, although limited in number.

In other embodiments, the IMD may employ two power sources, a first which is primary and a second which is rechargeable, that normally share the load for powering both the cardiac and neurostimulation circuits. The sources may be functionally in parallel but connected via a circuit that prevents the primary source from recharging the rechargeable source. The rechargeable source may be recharged, periodically (such as once a day) or as-needed basis responsive to voltage level or charge removed from battery in conjunction with patient notification that need a recharge is needed soon. If the recharge does not occur on a timely or sufficient basis, the rechargeable source becomes depleted and is disconnected from the circuit. The neurostimulation function may also or alternatively then be disabled. This approach extends the life of the primary source and the overall useful life of the device.

In yet other embodiments, a first primary source may be constantly connected to a rechargeable second source. The second source may have a higher discharge current capability and be able to deliver brief high power needs and then be recharged by the higher capacity but weaker discharge capability primary source. The sources remain functionally connected in parallel.

As noted above, use of power supplies other than batteries, for one or both of the power sources is useful in the context of the present invention. In this context, conventional capacitors, "supercapacitors" and the next generation "ultracapacitors" can provide a function similar to a rechargeable battery, but can often do it better. Faster recharge capability, smaller size, faster discharge current capability and a wider choice of output voltages are among the benefits. In such embodiments, the power sources may be one or a bank of capacitors in parallel or series or series/parallel. Super or ultracapacitors are describe, for example in U.S. Pat. No. 6,067,474 issued to Schulman, set al., U.S. Pat. No. 7,177,690 issued to Wood, et al. and U.S. Pat. No. 5,993,996 issued to Firsich, et al., all incorporated herein by reference in their entireties.

Use of a self-powered energy generator as one or both power sources is also useful in the context of the present invention. The power source may be a device that generates power from motion, temperature differentials, body chemistry, etc. This item can be integral to the cardiac/INS device or connected to it. This self-powered energy generator can be the sole power or have support components connected thereto such as a rechargeable battery or capacitor or super-capacitor, to store energy that is generated and serve as the power supply. Self powered generators are described, for example in U.S. Pat. No. 3,943,936, issued to Rasor, et al., U.S. Pat. No. 3,486,506 issued to Auphan, U.S. Pat. No. 3,563,245 issued to McLean, et al. US Patent Application Publication No. US 2008/0261085 A1, by Sastry, et al. (now abandoned) and US Patent Application Publication No. US 2008/0300660 A1, by Sasha, all incorporated herein by reference in their entireties.

The details of one or more embodiments are set forth in the accompanying drawings and the description below. Other features, objects, and advantages of the techniques of this disclosure will be apparent from the description and drawings, and from the claims.

DETAILED DESCRIPTION

As described herein, IMDs including both cardiac stimulation capability and neurostimulation capability may include more than one power source. In general, cardiac stimulation therapy may be considered more important to preserving the life of a patient than neurostimulation therapy. For example, cardiac stimulation therapy may correct a ventricular arrhythmia in a patient and prevent sudden cardiac arrest. For this reason, one power source may be dedicated to providing cardiac stimulation therapy, and a separate power source can provide power for a therapy that may not be considered critical to sustaining life (e.g. neurostimulation). Such a configuration preserves the battery dedicated for providing cardiac stimulation therapy even if the second power source is depleted. In this manner, the reliability of a cardiac stimulator can be maintained in an IMD that is configured to provide both cardiac stimulation and an electrical stimulation therapy such as neurostimulation. Further, the electrical stimulation therapy can be powered using a rechargeable power source such as a rechargeable battery such that such therapy is not limited to the power commonly available in a cardiac stimulator.

Figure 1:
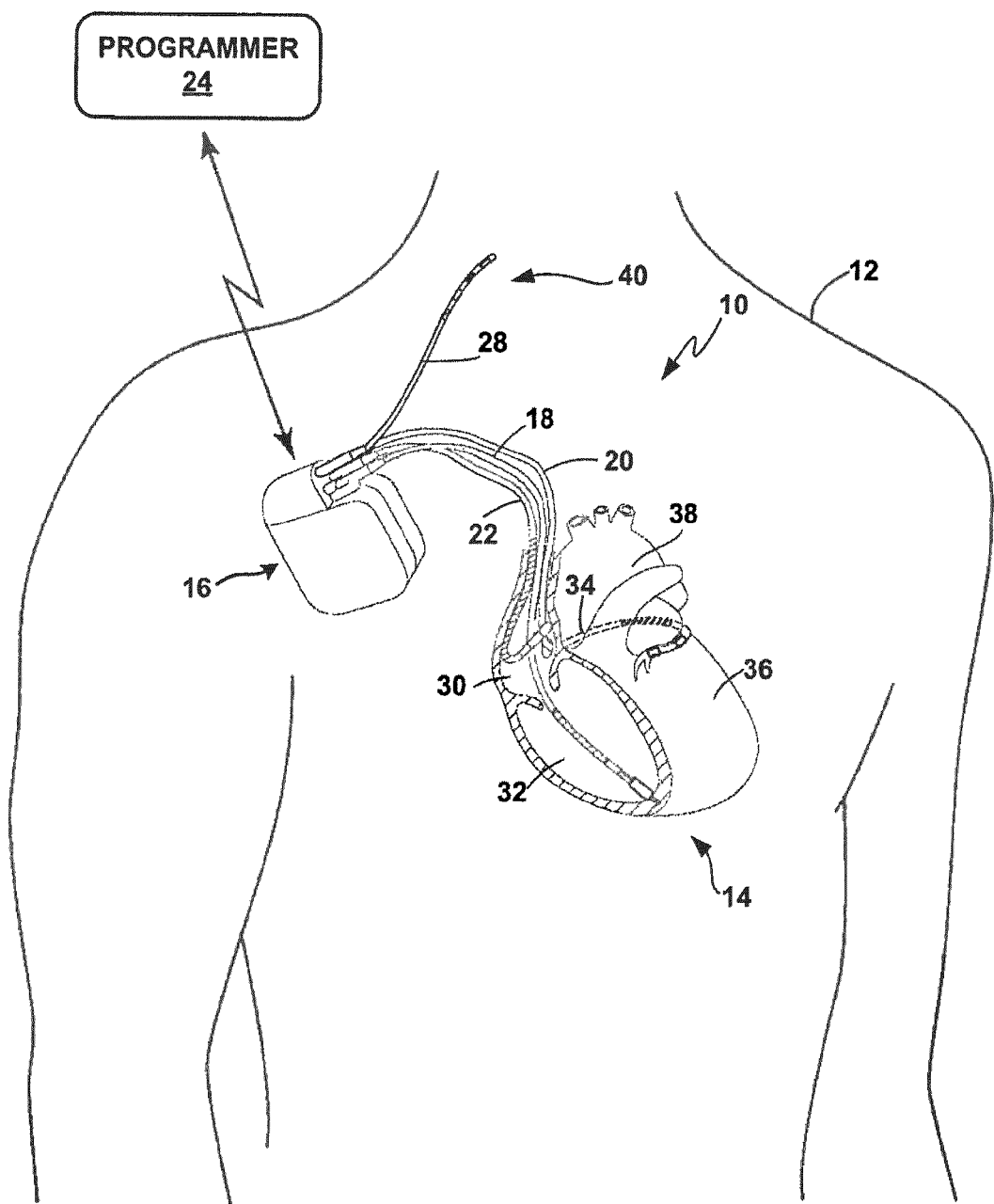
FIG. 1 is a diagram illustrating a therapy system configured to provide both neurostimulation and cardiac stimulation to a patient according to the present invention.
Figure 4:
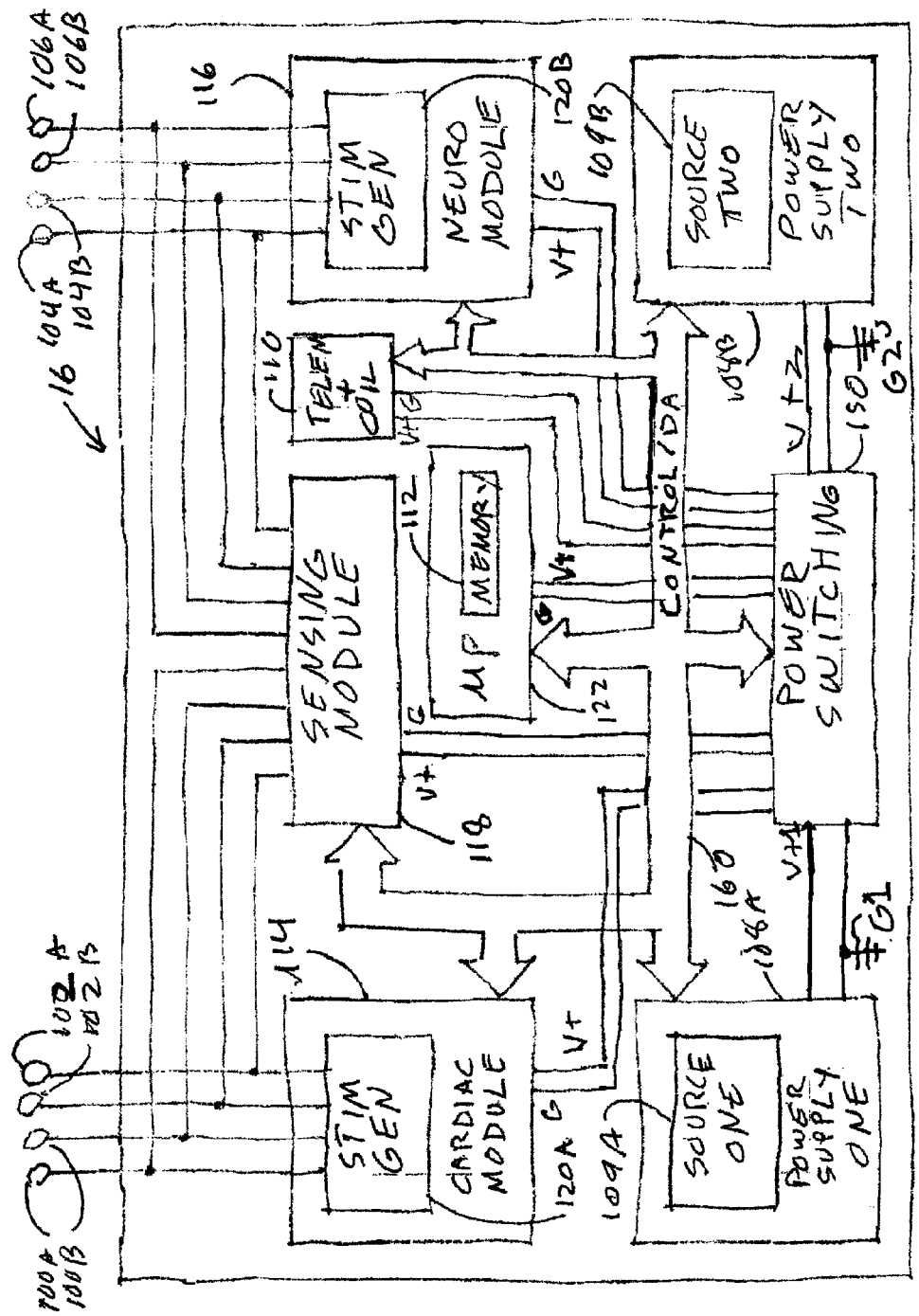
FIG. 4 is a functional schematic diagram of an IMD included in the therapy system shown in FIG. 1.

FIG. 1 is a conceptual diagram illustrating therapy system 10, which may be used to provide therapy to patient 12. Patient 12 ordinarily, but not necessarily, will be a human patient, although system 10 could find application in other living mammals or other living animals. Therapy system 10 includes IMD 16, which is coupled to leads 18, 20, 22, and 28. In addition therapy system 10 also includes programmer 24, which wirelessly communicates with IMD 16. IMD 16 may comprise a first therapy and/or sensing module and a second therapy and/or sensing module. In the example illustrated in FIG. 1, the first therapy and/or sensing module may comprise a neurostimulation module and the second therapy and/or sensing module may comprise a cardiac stimulation module, e.g., as shown in FIG. 4. In other words, the implantable medical device may include the neurostimulation module and the cardiac stimulation module within a common housing of IMD 16.

IMD 16 includes at least two power sources. For example, a first power source may be a power source dedicated to the operation of the cardiac stimulation module, while a second power source may be used to power at least the neurostimulation module. In addition, the second power source may be used for other non-essential functions like wireless telemetry, diagnostic data processing, etc.

Stimulation therapy provided by the cardiac stimulation module may be more important to preserving the life of patient 12. As compared to cardiac stimulation therapy such as pacing, cardioversion and/or defibrillation, neurostimulation therapy typically requires significantly more power over time. For this reason, the second power source may comprise a rechargeable power source; for example, the second power source may include an inductive coil to receive power transcutaneously and a rechargeable battery to store power. As another example, the second power source may comprise a power source optimized for delivering high frequency pacing pulses.

The cardiac stimulation module includes pacing, cardioversion, and/or defibrillation circuitry that provides electrical stimulation therapy to heart 14 of patient 12 via electrodes coupled to one or more of leads 18, 20, and 22. For example, pacing may include antitachycardia pacing (ATP) and/or Atrial-Synchronized biventricular pacing (Cardiac Resynchronization Therapy or CRT). In some examples, the cardiac stimulation module may deliver pacing pulses, but not cardioversion or defibrillation pulses, while in other examples, the cardiac stimulation module may deliver cardioversion or defibrillation pulses, but not pacing pulses. In addition, in further examples, the cardiac stimulation module may deliver pacing, cardioversion, and defibrillation pulses. Alternatively, or additionally, the cardiac stimulation module may also include circuitry for sensing cardiac signals from heart 14 of patient 12.

Leads 18, 20, 22 extend into heart 14 of patient 12 to sense electrical activity of heart 14 and/or deliver electrical stimulation to heart 14. In the example shown in FIG. 1, right ventricular (RV) lead 18 extends through one or more veins (not shown), the superior vena cava (not shown), and right atrium 30, and into right ventricle 32. Left ventricular (LV) coronary sinus lead 20 extends through one or more veins, the vena cava, right atrium 30, and into the coronary sinus 34 to a region adjacent to the free wall of left ventricle 36 of heart 14. Right atrial (RA) lead 22 extends through one or more veins and the vena cava, and into the right atrium 30 of heart 14. As shown in FIG. 1, the cardiac stimulation module is coupled to three leads, e.g. leads 18, 20, and 22. However, in some aspects, the cardiac stimulation module may be coupled to more or fewer leads. In other examples, the cardiac stimulation module of IMD 16 may deliver electrical stimulation therapy to heart 14 by delivering stimulation to an extravascular tissue site in addition to or instead of delivering stimulation via electrodes of intravascular leads 18, 20, 22.

The cardiac stimulation module of IMD 16 may sense electrical signals attendant to the depolarization and repolarization of heart 14 via electrodes (not shown in FIG. 1) coupled to at least one of the leads 18, 20, 22. In some examples, the cardiac stimulation module provides pacing pulses to heart 14 based on the electrical signals sensed within heart 14. These electrical signals sensed within heart 14 may also be referred to as cardiac signals. The configurations of electrodes used by the cardiac stimulation module for sensing and therapy delivery may be unipolar or bipolar. The cardiac stimulation module may also provide defibrillation therapy and/or cardioversion therapy via one or more electrodes located on at least one of the leads 18, 20, 22 and also the housing of IMD 16. For example, the cardiac stimulation module may detect arrhythmia of heart 14, such as fibrillation of ventricles 32 and 36, and deliver defibrillation therapy to heart 14 in the form of electrical pulses. In some examples, the cardiac stimulation module may be programmed to deliver a progression of therapies, e.g., pulses with increasing energy levels, until a fibrillation of heart 14 is stopped. The cardiac stimulation module may detect fibrillation employing one or more fibrillation detection techniques known in the art. In some instances, the cardiac stimulation module of IMD 16 may not provide any stimulation. In further instances, the neurostimulation module of IMD 16 may include both sensing and therapy delivery functionality.

The neurostimulation module may be any suitable circuitry for generating electrical stimulation that may be delivered to a tissue site of patient 12 via electrodes of lead 28. As such, the neurostimulation module of IMD 16 is coupled to lead 28. The tissue site of patient 12 may be a nerve or other extravascular tissue site of patient 12, e.g., proximate a vagus nerve, a spinal cord or heart 14 of patient 12. In some examples, the neurostimulation module may deliver electrical stimulation that is delivered to peripheral nerves that innervate heart 14, or fat pads on heart 14 that may contain nerve bundles. The neurostimulator may deliver stimulation to an extravascular tissue site and/or tissue proximate a nerve via lead 28, which may or may not be extravascular. That is, in some cases, the tissue proximate the nerve may be an extravascular tissue site. In other cases, lead 28 may be positioned within vasculature and provide stimulation to a tissue site proximate a nerve through the wall of the vein, artery, or other vasculature (not shown). In addition, the extravascular tissue site may or may not be proximate a nerve. In the example shown in FIG. 1, electrodes of lead 28 are positioned to deliver electrical stimulation to a vagus nerve (not shown in FIG. 1) of patient 12. The stimulation delivered by the neurostimulation module or cardiac stimulation module may take the form of stimulation pulses or continuous waveforms, and may be characterized by controlled voltage levels or controlled current levels, as well as pulse width and pulse rate in the case of stimulation pulses.

In the example of FIG. 1, the neurostimulation module of IMD 16 provides a programmable stimulation signal (e.g., in the form of electrical pulses or a continuous signal) delivered to target stimulation site 40 by implantable medical lead 28, and more particularly, via one or more stimulation electrodes carried by lead 28. The neurostimulation module may also be referred to as a signal generator, stimulation generator or an electrical stimulator. Furthermore, in some embodiments, the neurostimulation module may be coupled to two or more leads, e.g., for bilateral or multi-lateral stimulation, e.g., as illustrated in FIG. 4.

Although the neurostimulation module of IMD 16 is sometimes referred to as a "neurostimulator" and described as delivering neurostimulation pulses, the neurostimulation module may deliver other types of electrical stimulation to any suitable tissue site within patient 12, which may or may not be proximate a nerve. In some examples, lead 28 may also carry one or more sense electrodes to permit the neurostimulation module to sense electrical signals, e.g., neurological signals, from target stimulation site 40. In this case, the neurostimulation module of IMD 16 may not provide any stimulation. In further instances, the neurostimulation module of IMD 16 may include both sensing and therapy delivery functionality.

In some examples, the neurostimulation module and cardiac stimulation module of IMD 16 may provide therapy to patient 12 in conjunction with one another. For example, delivery of electrical stimulation by the neurostimulation module within IMD 16 to one or more extravascular target tissue sites proximate to a nerve, nerve site, cardiac fat pad, or another extravascular target tissue site (i.e., tissue site that is not implanted within heart 14 or within an artery or other vasculature of patient 12) may provide cardioprotective benefits to patient 12. For example, delivery of electrical stimulation to the extravascular tissue site may help reduce or eliminate cardiovascular conditions such as tachycardia, A-V dissociation, brachycardia, ischemia, inefficient heart pumping, inefficient collateral circulation of heart 14 or cardiac muscle trauma. In addition, delivery of electrical stimulation by the neurostimulation module may augment antitachycardia pacing by the cardiac stimulation module or provide back-up therapy to the cardiac stimulation module. For example, if the cardiac stimulation module is unavailable to provide therapy to patient 12, e.g., due to a low power level, the neurostimulation module may deliver therapy to patient 12 to help terminate or prevent a cardiac event (e.g., tachycardia). In other examples, the neurostimulation module may deliver electrical stimulation to patient 12 independently of the electrical stimulation delivered by the cardiac stimulation module.

In the example shown in FIG. 1, target stimulation site 40 may be a parasympathetic nerve, such as a vagus nerve, of patient 12. Stimulation of a parasympathetic nerve of patient 12 may help slow intrinsic rhythms of heart 14, which may both facilitate antitachyarrhythmia therapy (e.g., antitachycardia pacing, cardioversion or defibrillation) delivered by the cardiac stimulation module. For example, stimulation of a sympathetic nerve of patient 12 may help reduce the incidence of tachyarrhythmia of heart 14.

In other examples, electrodes of lead 28 may be positioned to deliver electrical stimulation to any other suitable nerve, organ, muscle or muscle group in patient 12, which may be selected based on, for example, a therapy regimen selected or prescribed for a particular patient. In some examples, the neurostimulation module may deliver electrical stimulation to other parasympathetic nerves, baroreceptors, the carotid sinus or a cardiac branch of the vagal trunk of patient 12 in order to facilitate the delivery of therapy by the cardiac stimulation module.

As another example, lead 28, which is connected to neurostimulation module of IMD 16, may be positioned to deliver electrical stimulation to the spinal cord of a patient. Stimulation of a spinal cord or nerves branching therefrom by the neurostimulation module may help prevent or mitigate occurrences of tachyarrhythmias. In this way, the cardiac stimulation module and neurostimulation module may operate in conjunction with each other to help prevent arrhythmias, as well as to terminate detected arrhythmias.

The neurostimulation module may deliver electrical stimulation to patient 12 independently of the electrical stimulation delivered by the cardiac stimulation module. For example, the neurostimulation module may be used with a variety of different therapies, such as peripheral nerve stimulation (PNS), peripheral nerve field stimulation (PNFS), deep brain stimulation (DBS), cortical stimulation (CS) and the like. The stimulation may be configured to alleviate a variety of symptoms or conditions such as chronic pain, tremor, Parkinson's disease, or epilepsy.

Again, in some cases, the cardiac stimulation module and the neurostimulation module within IMD 16 may function in conjunction with one another to provide effective cardiac therapy to patient 12. In other cases, the cardiac stimulation module and neurostimulation module may function independently of one another to provide therapy to patient 12. For example, if patient 12 suffers from a cardiac condition and neurological condition, the cardiac stimulation module and neurostimulation module may function independently to alleviate the cardiac and neurological conditions. Moreover, though IMD 16 is described as providing therapy for cardiac and neurological conditions, aspects of this disclosure are not so limited. In some aspects, IMD 16 may provide electrical stimulation to provide relief from urinary or fecal incontinence, sexual dysfunction, obesity, or gastroparesis, as well as provide relief for cardiac or neurological conditions or both.

Figure 2:
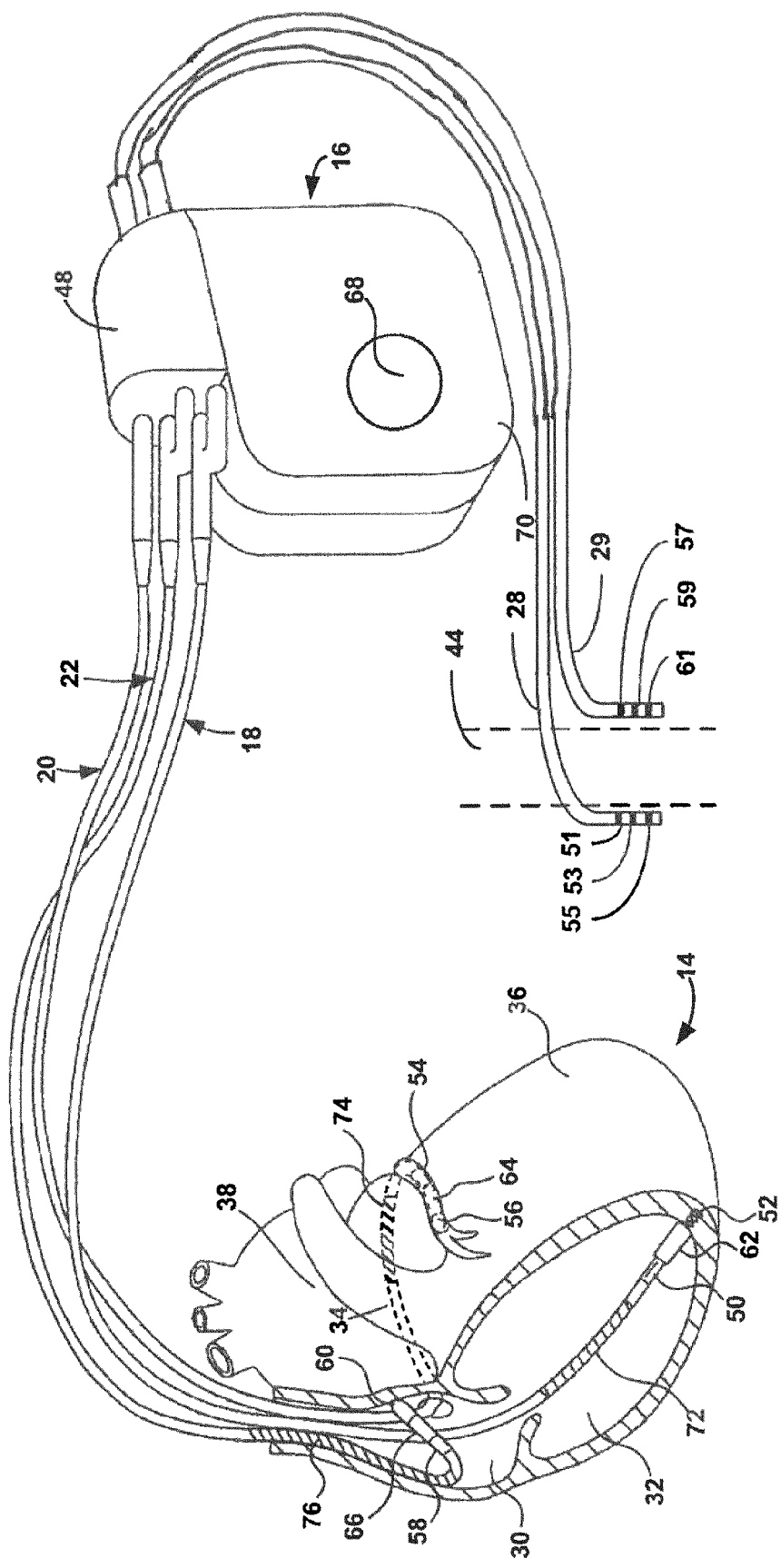
FIG. 2 is a diagram illustrating the IMD of FIG. 1 and the medical leads in greater detail.

FIG. 2 is a conceptual diagram illustrating cardiac module within IMD 16 and leads 18, 20, 22, 28, and 29 of therapy system 10 in greater detail. Leads 18, 20, 22 may be electrically coupled to a stimulation generator, a sensing module, or other modules of a cardiac module within IMD16 via connector block 48. In this embodiment, Leads 28 and 29 may be coupled to a stimulation generator, a sensing module, or other modules of a electrical stimulation module within IMD 16 via ports in connector block 48 located opposite those receiving leads 18, 20 and 22. The orientation of the connector ports on the IMD 16 may be selected as a function of the intended location of the various leads. As shown in FIG. 2, leads 18, 20, and 22 couple heart 14 of patient 12, and leads 28 and 29 couple to spinal cord 44 of patient 12. In some examples, proximal ends of leads 18, 20, 22, 28, and 29 may include electrical contacts that electrically couple to respective electrical contacts within respective connector blocks 47, 48. In addition, in some examples, leads 18, 20, 22, 28, and 29 may be mechanically coupled to connector block 48 with the aid of set screws, connection pins or another suitable mechanical coupling mechanism.

Each of the leads 18, 20, 22, 28, and 29 may include an elongated insulative lead body, which may carry a number of concentric coiled conductors separated from one another by tubular insulative sheaths. In the illustrated example, bipolar electrodes 50 and 52 are located proximate to a distal end of lead 18. In addition, bipolar electrodes 54 and 56 are located proximate to a distal end of lead 20 and bipolar electrodes 58 and 60 are located proximate to a distal end of lead 22. Similarly, electrodes 51, 53, and 55 are located at proximate to a distal end of lead 28, and electrodes 57, 59, and 61 are located proximate to a distal end of lead 29.

Electrodes 50, 54, 56 and 60 may take the form of ring electrodes, and electrode 52 may take the form of an extendable helix tip electrode mounted retractably within insulative electrode head 62. Each of the electrodes 50, 52, 54, 56, 58, and 60 may be electrically coupled to a respective one of the coiled conductors within the lead body of its associated lead 18, 20, 22, and thereby coupled to respective ones of the electrical contacts on the proximal end of leads 18, 20 and 22. Similarly, electrodes 51, 53, 55, 57, 59, and 61 may be comprise ring electrodes or other type of electrodes and electrically couple to a respective one of the coiled conductors within the lead body of its associated lead 28, 29.

Electrodes 50, 52, 54, 56, 58, and 60 may sense electrical signals attendant to the depolarization and repolarization of heart 14. The electrical signals are conducted to the cardiac module within IMD 16 via the respective leads 18, 20, 22. In some examples, the cardiac module also delivers pacing pulses via electrodes 50, 52, 54, 56, 58, and 60 to cause depolarization of cardiac tissue of heart 14. In some examples, as illustrated in FIG. 2, the cardiac module includes one or more housing electrodes, such as housing electrode 68, which may be formed integrally with an outer surface of hermetically-sealed housing 70 of IMD 16 or otherwise coupled to housing 70. As described above, housing 70 may provide the ground for the power source and the various components within the cardiac module and electrical stimulation module within IMD 16. In some examples, housing electrode 68 is defined by an uninsulated portion of an outward facing portion of housing 70 of IMD 16. Other division between insulated and uninsulated portions of housing 70 may be employed to define two or more housing electrodes. In some examples, housing electrode 68 comprises substantially all of housing 70. Any of the electrodes 50, 52, 54, 56, 58, and 60 may be used for unipolar sensing or pacing in combination with housing electrode 68. As described in further detail with reference to FIG. 4, housing 70 may enclose a stimulation generator that generates cardiac pacing pulses and defibrillation or cardioversion shocks, as well as a sensing module for monitoring the patient's heart rhythm.

Electrodes 51, 53, 55, 57, 59, and 61 may provide stimulation to spinal cord 44 or alternatively sense signals proximate to spinal cord 44. The electrical signals are conducted to the cardiac module within IMD 16 via the respective leads 28 and 29. In some examples, the electrical stimulation module delivers stimulation pulses via electrodes 51, 53, 55, 57, 59, and 61 to cause stimulation on spinal cord 44. Electrodes 51, 53, 55, 57, 59, and 61 may be fabricated from any suitable electrically conductive and biocompatible material, such as, but not limited to, platinum, platinum alloy or other materials.

Leads 18, 20, 22 also include elongated electrodes 72, 74, 76, respectively, which may take the form of coils. The cardiac module within IMD 16 may deliver defibrillation pulses to heart 14 via any combination of elongated electrodes 72, 74, 76, and housing electrode 68. Electrodes 68, 72, 74, 76 may also be used to deliver cardioversion pulses to heart 14. In addition, electrodes 68, 72, 74, 76 may also be used as sensing electrodes, e.g., to sense EGM waveform data. Electrodes 72, 74, 76 may be fabricated from any suitable electrically conductive and biocompatible material, such as, but not limited to, platinum, platinum alloy or other materials known to be usable in implantable defibrillation electrodes.

The configuration of the therapy systems 10 illustrated in FIGS. 1 and 2 are merely examples. In other examples, a therapy system may include epicardial leads and/or patch electrodes instead of or in addition to the transvenous leads 18, 20, 22, 28, and 29 illustrated in FIG. 2. Further, IMD 16 need not be implanted within patient 12. In examples in which IMD 16 is not implanted in patient 12, the cardiac module within IMD 16 may deliver defibrillation pulses and other therapies to heart 14 via epicardial leads that extend through the skin of patient 12 to a variety of positions within or outside of heart 14. In examples in which IMD 16 is not implanted in patient 12, the electrical stimulation module within IMD 16 may deliver electrical stimulation to target tissue sites within patient 12 via external electrodes or via percutaneous leads that extend through the skin of patient 12.

In other examples of therapy systems that provide electrical stimulation therapy to heart 14, a therapy system may include any suitable number of leads coupled to the cardiac module within IMD 16, and each of the leads may extend to any location within or proximate to heart 14. For example, other examples of therapy systems may include three transvenous leads located as illustrated in FIGS. 1 and 2, and an additional lead located within or proximate to left atrium 38. As another example, other examples of therapy systems may include a single lead that extends from the cardiac module within IMD 16 into right atrium 30 or right ventricle 32, or two leads that extend into a respective one of the right ventricle 32 and right atrium 30. In another example, one or more of the leads may not be located within the heart, but instead outside and proximate to heart 14.

Similarly, in examples of therapy systems that provide electrical stimulation therapy to spinal cord 44, a therapy system may include any suitable number of leads coupled to the electrical stimulation module within IMD 16, and each of the leads may extent to any location within or proximate to spinal cord 44. Furthermore, in some examples, the electrical stimulation module may provide stimulation to extravascular tissue. In such examples, each of the leads may extent to any location within or proximate to the extravascular tissue. The neurostimulator may deliver stimulation to an extravascular tissue site and/or tissue proximate a nerve, which may or may not be extravascular. That is, in some cases, the tissue proximate the nerve may be an extravascular tissue site. In other cases, the lead may be positioned within vasculature and provide stimulation to a tissue site proximate a nerve through the wall of the vein, artery, or other vasculature. In addition, the extravascular tissue site may or may not be proximate a nerve.

Figure 3:
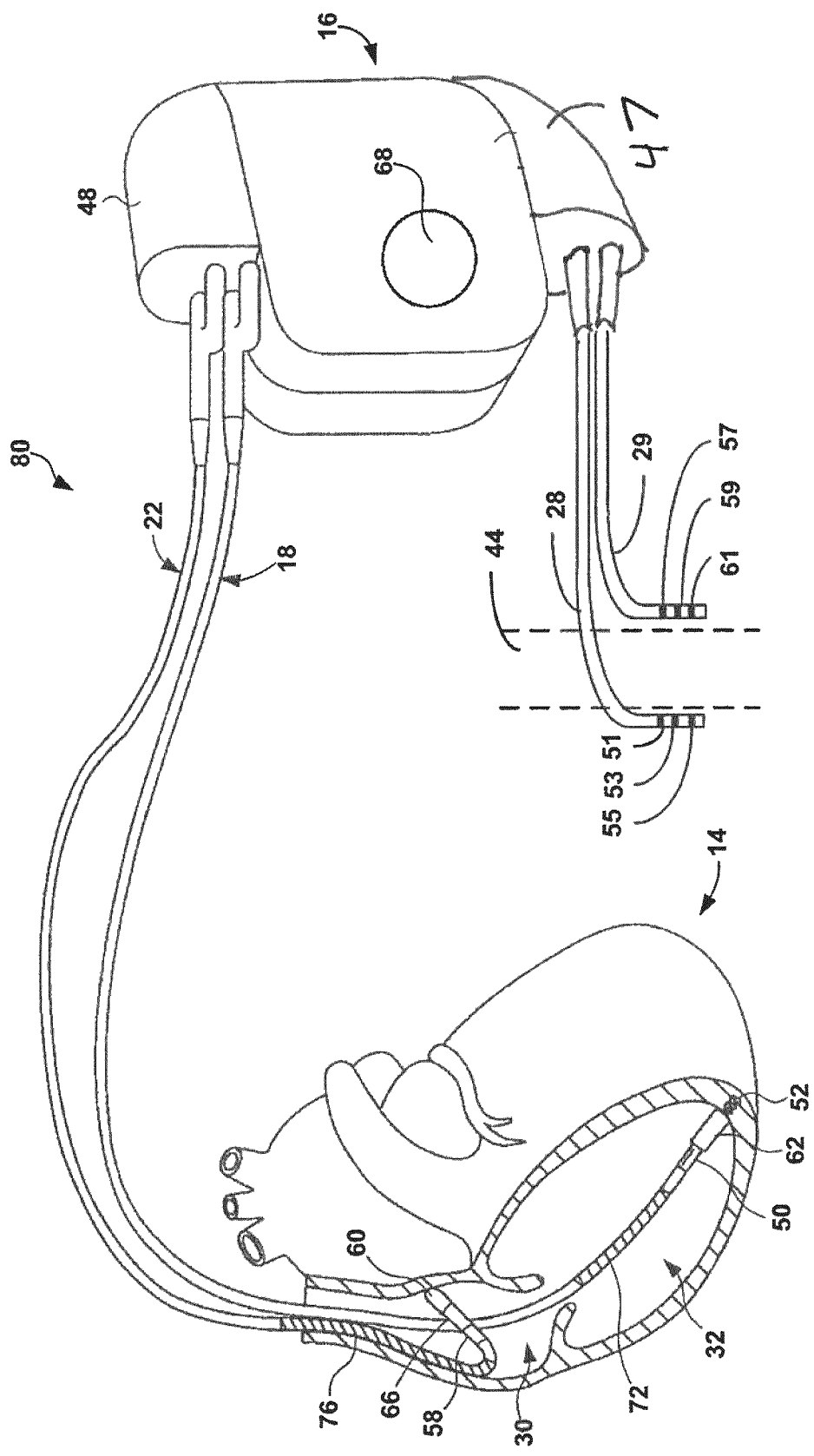
FIG. 3 is a diagram illustrating another view of an IMD and medical leads.

FIG. 3 is a conceptual diagram illustrating another example of therapy system 80, which is similar to therapy system 10 of FIG. 1, but includes two cardiac leads 18, 22, rather than three leads. Leads 18, 22 are implanted within right ventricle 32 and right atrium 30, respectively. Therapy system 80 shown in FIG. 3 may be useful for providing defibrillation and pacing pulses to heart 14. Therapy system 80 may further include the electrical stimulation module within IMD 16 which is configured to deliver electrical stimulation therapy to one or more nerves or spinal cord 44 of patient 14 in order to help prevent or mitigate an arrhythmia of patient 12. Unlike the system illustrated in FIG. 2, leads 28 and 29 are coupled to electrical stimulation module within IMD 16 via a second connector block 47.

FIG. 4 is an exemplary functional block diagram of IMD 16, in which the various embodiments of the present invention may be practiced. IMD 16 includes power supplies 108A, 108B, telemetry/inductive coil 110, cardiac stimulation module 114, neurostimulation module 116, sensing module 118 and processor 122 including memory 112. Cardiac module 114 includes stimulation generator 120A, which provides stimulation via electrodes 100A, 100B, 102A, and 102B. Neurostimulation module 116 includes stimulation generator 120B, which provides stimulation via electrodes 104A, 104B, 106A, and 106B. Processor 122 controls therapies of both cardiac module 114 and neurostimulation module 116. Cardiac module 114 and neurostimulation module 116 include stimulation circuits 120A and 120 B which include pulse generation circuits and switching circuits for selecting which electrodes are used to deliver stimulation pulses. Processor 122 receives inputs from and delivers control signals to the stimulation modules and power supplies as well as sensing module 118 and power switching module 150. The inputs from sensing module 118 may be used by the processor, for example, to select, control, or adjust the therapies provided by cardiac module 114 and neurostimulation module 116. Switching module 150 operates under processor control to selectively activate and deactivate the power supplies and to control which of the power supplies is employed to power the rest of the components of the device, according to the various embodiments of the invention. For purposes of the present disclosure, it should be understood that switching circuitry 150 has the capability of selectively coupling and decoupling both the power (V+) and ground (G) lines of the components of the device to the desired power supply outputs (V+1, V+2) and power supply grounds (G1, G2) to provide connection and/or isolation of the components and power sources as described herein. It should also be understood that in some embodiments of the invention, the switching circuitry may be unnecessary. For example, in some simpler embodiments in which a first power supply is dedicated only to the cardiac stimulation circuitry and a second only to the neurostimulation circuitry, the switching circuitry may be deleted and disablement of the neurostimulation circuitry responsive to the depletion of the second power source may be accomplished without the need for changing interconnections of the power supply circuits. The switching circuitry is included in the exemplary drawing of FIG. 3 primarily as it relates to embodiments as discussed above in which the second power source may also be selectively coupled to the cardiac stimulation circuitry and/or temporarily coupled to the first power source, as discussed above.

Sensing module 118 monitors signals from at least one of electrodes 100A, 100B, 102A, 102B, 104A, 104B, 106A and 106B in order to monitor electrical activity of heart 14, e.g., via an electrogram (EGM) signal, such as an electrocardiogram (ECG) signal. Sensing module 118 may include a switching circuitry for selecting a particular subset of available electrodes to sense the heart activity. Sensing module 118 may also monitor signals from a target neurostimulation site, such as target site 44 (FIG. 1). Sensing module 118 may also measure lead impedance or other tissue measurements that aid a clinician to generate effective therapy programs for both cardiac stimulation module 114 and neurostimulation module 116. While not illustrated, it is also envisioned that some embodiments of the invention may also include physiologic sensors such as pressure sensors, activity sensors and the like, much as presently included in implantable cardiac stimulation and monitoring devices.

Processor 122 controls stimulation generator 120A to deliver stimulation therapy to heart 14 according to a selected one or more of therapy programs, which may be stored in memory 112. For example, stimulation generator 120A may deliver pacing, cardioversion or defibrillation therapy. Processor 122 also controls stimulation generator 120B to deliver stimulation therapy to therapy stimulation site 40, which may be, e.g., a vagus nerve of patient 12. As previously mentioned, in other examples, stimulation generator 120B may be configured to deliver neurostimulation to a variety of sites within patient 12. Processor 122 controls stimulation generator 120A and stimulation generator 120B to deliver electrical pulses with the amplitudes, pulse widths, frequency, or electrode polarities specified by the selected one or more therapy programs. Processor 122 may also monitor power supplies 109A, 109B to determine if a recharge or replacement is necessary.

Processor 122 may include any one or more of a microprocessor, a controller, a digital signal processor (DSP), an application specific integrated circuit (ASIC), a field-programmable gate array (FPGA), or equivalent discrete or integrated logic circuitry. In some examples, processor 122 may include multiple components, such as any combination of one or more microprocessors, one or more controllers, one or more DSPs, one or more ASICs, or one or more FPGAs, as well as other discrete or integrated logic circuitry. The functions attributed to processor 122 herein may be embodied as software, firmware, hardware or any combination thereof.

Processor 122 sends and receives information via telemetry/inductive coil 110. For example, telemetry/inductive coil 110 provides a communication interface with programmer 24 (FIG. 1) and/or other computing devices. Processor may send data including historical sensing data as well as historical therapy data via telemetry/inductive coil 110 to programmer 24 (FIG. 1) and/or other computing devices. In addition, processor 122 may receive updates to programs, including cardiac stimulation and neurostimulation parameters such as amplitude and electrode combinations, from programmer 24. Such information may be stored in memory 112.

Memory 112 includes computer-readable instructions that, when executed by processor 122, cause processor 122 to perform the functions described herein associated with the various embodiments of the present invention. Memory 112 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

As shown in FIG. 4, IMD 16 includes two power sources: first power supplies 108A and 108B. First power supply 108A includes power source 109A, while second power supply 108B includes power source 109B.

As described above, in some embodiments, first power supply 108A is normally dedicated to powering cardiac stimulation module 114 including stimulation generator 120A. while second power supply 108B powers neurostimulation module 116 including stimulation generator 120B.

In other embodiments, second power supply 108B may normally also power cardiac stimulation module 114. In such examples, first power supply 108A may serve as a back-up power source for cardiac stimulation module 114 in the event that second power supply 108B is depleted. In such embodiments, power source 108B can be used to supply power to neurostimulation module 116 and cardiac stimulation module 114, whereas first power source 108A may only be used to supply power to As referred to herein, supplying power to cardiac stimulation module 114 also includes supplying power to any other components of IMD 16 as necessary for the functionality of cardiac stimulation module 114. Such functionality may include monitoring cardiac signals from the heart of patient 12 as well as recall of therapy programs from memory 112 and control of cardiac stimulation module 114 by processor 122. In this manner, the functionality of cardiac stimulation module 114 may rely upon processor 122, memory 112, and possibly sensing module 118. For this reason, first power source 108A should not be considered to be electrically isolated from processor 122, memory 112 or sensing module 118.

Neurostimulation module 116 may consume significantly more power over time to provide neurostimulation therapy than cardiac stimulation module 114 consumes to provide cardiac stimulation therapy. For this reason, source 109B could be a rechargeable battery. For example, source 109B may be recharged transcutaneously via telemetry/inductive coil 110. In such examples, battery 109B may be a lithium ion battery, a lithium polymer battery, a supercapacitor or other rechargeable battery. In alternate examples, second power source 108B may not include a battery, but instead rely directly upon transcutaneous inductive power transmissions via telemetry/inductive coil 110. Telemetry/inductive coil 110 may receive power from an external power supply carried or worn by patient 12.

In contrast, source 109A may a non-rechargeable battery. In such examples, battery 109A may be a lithium battery having a lithium metal anode material. Alternatively, source 109A may be a rechargeable battery and rechargeable transcutaneously via telemetry/inductive coil 110. In such examples, source 109A may be a lithium ion battery, a lithium polymer battery or other rechargeable battery. A non-rechargeable battery may be selected to last for several years, while a rechargeable battery may be inductively charged from an external device, e.g., on a daily or weekly basis.

In some embodiments, the grounds of sources 109A, 109B may be electrically isolated from one another. For example, sources 109A, 109B may be electrically isolated using magnetic isolation via a transformer or optoisolation through light-emitting diodes (LEDs). In other examples, isolation techniques, such as low-pass filters may be used to separate one or more of sources 109A, 109B and discrete components forming, telemetry/inductive coil 110, memory 112, cardiac stimulation module 114, neurostimulation module 116, sensing module 118 and processor 122. As another example, IMD 16 may include separate memory, processors and sensing modules for cardiac stimulation module 114 and neurostimulation module 116. These techniques may mitigate interference and cross-talk between the cardiac stimulation, neurostimulation and sensing functionalities of IMD 16.

Telemetry/inductive coil 110 is described as having the dual function of receiving data as well as inductive power. However, these functions may also be accomplished using separate components rather than a common coil. For example, data transfer may occur using any suitable techniques such as other types of wireless communication.

In addition, while IMD 16 is described as having exactly two power sources, other examples may include more than two power sources. For example, an IMD may include more than two stimulation modules, each with a separate power source. As another example, sensing circuitry and/or telemetry circuitry of an IMD may include a separate power source. Other power source configurations are also possible.

Figure 5:
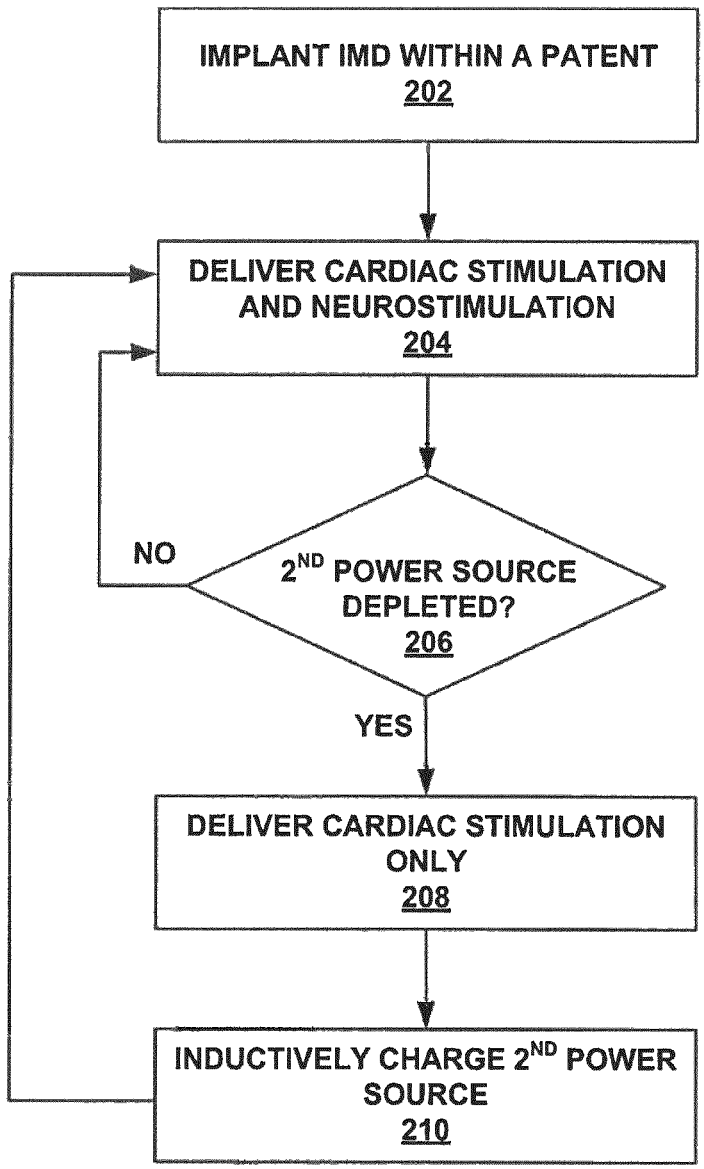
FIG. 5 is a flowchart illustrating techniques for delivering both neurostimulation and cardiac stimulation to a patient.

FIG. 5 is a flowchart illustrating techniques for delivering stimulation therapy including both neurostimulation and cardiac stimulation to a patient. For clarity, the techniques illustrated in FIG. 5 are described with respect to therapy system 10 (FIG. 1) including IMD 16 as shown in FIG. 4. The flowchart of FIG. 5 includes the general functions controlled by processor 122 by means of instructions stored in memory 122.

First, IMD 16 and medical leads 18, 20, 22 and 28 are implanted within patient 12 (202). Next, IMD 16 begins stimulation therapy. Specifically, under control of processor 122, cardiac stimulation module 114 delivers cardiac stimulation therapy, while neurostimulation module 116 delivers neurostimulation therapy (204). Delivery of cardiac stimulation therapy and neurostimulation therapy may include alternating periods of sensing physiological data from patient 12 in combination with delivering stimulation therapy signals via medical leads 18, 20, 22 and 28. In addition, sensing module 118 may stop sensing cardiac signals during periods of active neurostimulation as neurostimulation may interfere with the cardiac signals. In this manner, delivery of cardiac stimulation therapy and neurostimulation therapy does not necessarily mean simultaneous activity by both cardiac stimulation module 114 and neurostimulation module 116, but may instead be a coordinated therapy delivery between cardiac stimulation module 114 and neurostimulation module 116 as controlled by processor 122. Other techniques for the combined delivery of cardiac stimulation therapy and neurostimulation therapy are also possible.

During the combined delivery of cardiac stimulation therapy and neurostimulation therapy, processor 122 periodically determines if second power supply 109B is depleted (206). If second power source 109B is not depleted, IMD 16 continues both cardiac stimulation therapy and neurostimulation therapy (204). If second power source 109B is depleted, processor 122 may cause cessation of delivery of neurostimulation therapy and thereafter enable only delivery of cardiac stimulation therapy by drawing on power in first power supply 108A (208). Switching between power supplies is controlled by processor 122 via power switching module 150. Neurostimulation therapy resumes once patient 12 or a clinician charges second power source 108B, e.g., by placing an external inductive power source in proximity to telemetry/inductive coil 110 (21). In other embodiments, the functionality of neurostimulation module 116 may rely directly upon the presence of adequate power in second power source 109B. In such an example, processor 122 would not need to periodically determine if second power source 108B is depleted as neurostimulation would cease without intervention by processor 122 as soon as second power source 109B is depleted.

Processor 122 may also control functions of the power supplies and stimulation modules according to any of the variant embodiments described above in the Summary section, under control of the instructions stored in memory 112.

In one disclosed alternative embodiment discussed above power supply108A is employed to recharge power supply 108B, by connecting through 150 to Power Supply Two. In this embodiment, the engagement of this temporary recharge can optionally be synchronized, to minimize issues associated with commonality during recharge. For example, the recharge can occur during times when the crosstalk issues are of least impact, such as during blanking periods of cardiac module. Alternatively the recharge can occur during times when no high energy cardiac therapy is underway. In the context of the general flow-chart of FIG. 5, this operation should be understood to occur during Step 204, and continue for only a limited period. For example the software in memory 112 may instruct the microprocessor 122 to allow only a defined number of recharges or to allow recharges to occur only until power source 109A has reached a defined level of depletion. Thereafter, when the second power source has been re-depleted at 206, only the cardiac stimulation therapy is enabled at 208.

As an additional alternative, rather than temporary recharge of source 109B from source 109A, Source 109 A may temporarily provide power to both stimulation modules with the neurostimulation module only getting power under the circumstances discussed above for timing of the temporary recharges. In this alternative approach, power source 109A may at least intermittently supply the neurostimulation module when power source 109B is depleted, but remains isolated from power source 109B and the neurostimulation module 116 at times when commonality is suitable.

The techniques described in this disclosure are describe in the exemplary embodiment of FIG. 4 as controlled by processor 122 as defined in the instruction set stored in memory 112. However, the functionality of embodiments according to the invention may also be usefully implemented, in any convenient combination of hardware, software and/or firmware. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry. Correspondingly, While the control techniques described herein are primarily described as being performed by processor 122 any one or more parts of the techniques described herein may be implemented by a processor of one of the cardiac or neurostimulation modules or another computing device, alone or in combination with the cardiac or neurostimulation modules.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various aspects of the disclosure have been described. These and other aspects are within the scope of the following claims.

What is claimed is:

1. An implantable medical device (IMD) comprising:
a cardiac stimulation module which provides at least one stimulation therapy selected from a group consisting of:
pacing;
cardioversion; and
defibrillation;
an electrical stimulation module which provides electrical stimulation therapy;
a first power source, wherein the first power source provides power to the cardiac stimulation module and not to the electrical stimulation module; and
a second power source, wherein the second power source provides power to at least the electrical stimulation module.

2. The IMD of claim 1, wherein the first power source is a lithium battery.

3. The IMD of claim 1, wherein the first and second power sources both comprise batteries.

4. The IMD of claim 1, wherein the second power source includes an inductive coil configured to receive inductive power transcutaneously.

5. The IMD of claim 1, wherein the first power source is a first rechargeable battery, wherein the second power source includes a second rechargeable battery, the IMD further comprising an inductive coil that supplies power to recharge the first and second rechargeable batteries.

6. The IMD of claim 1, further comprising a housing containing the cardiac stimulation module, the electrical stimulation module and the first and second power sources.

7. The IMD of claim 1, further comprising means for mitigating interference and cross-talk between the cardiac stimulation module and the electrical stimulation module.

8. The IMD of claim 1, further comprising a processor that monitors the first power source and the second power source to determine when one or both of the first power source and the second power source is depleted.

9. The IMD of claim 8, wherein the processor supplies power to the cardiac stimulation module from the second power source only when the first power source is depleted.

10. An implantable medical device (IMD) comprising:
a cardiac stimulation module which provides at least one stimulation therapy selected from a group consisting of:
pacing;
cardioversion; and
defibrillation;
an electrical stimulation module which provides electrical stimulation therapy;
a first power source, wherein the first power source provides power to the cardiac stimulation module and not to the electrical stimulation module; and
a second power source, wherein the second power source provides power to at least the electrical stimulation module;
wherein the first power source comprises a non-rechargeable source, wherein the second power source comprises a rechargeable source.

11. The IMD of claim 10, wherein the rechargeable source is selected from a group consisting of:
a supercapacitor;
a lithium ion battery; and
a lithium polymer battery.

12. The IMD of claim 10, further comprising an inductive coil that supplies power to recharge the rechargeable source.

13. An implantable medical device (IMD) comprising:
a cardiac stimulation module which provides at least one stimulation therapy selected from a group consisting of:
pacing;
cardioversion; and
defibrillation;
an electrical stimulation module which provides electrical stimulation therapy;
a first power source, wherein the first power source provides power to the cardiac stimulation module and not to the electrical stimulation module; and
a second power source, wherein the second power source provides power to at least the electrical stimulation module;
wherein the electrical stimulation module is configured to deliver neurostimulation.

14. An implantable medical device (IMD) comprising:
a cardiac stimulation module which provides at least one stimulation therapy selected from a group consisting of:
pacing;
cardioversion; and
defibrillation;
an electrical stimulation module which provides electrical stimulation therapy;
a first power source, wherein the first power source provides power to the cardiac stimulation module and not to the electrical stimulation module; and
a second power source, wherein the second power source provides power to at least the electrical stimulation module;
wherein the second power source also provides power to the cardiac stimulation module.

15. An implantable medical device (IMD) comprising:
a cardiac stimulation module which provides at least one stimulation therapy selected from a group consisting of:

pacing;
cardioversion; and
defibrillation;
an electrical stimulation module which provides electrical stimulation therapy;
a first power source, wherein the first power source provides power to the cardiac stimulation module and not to the electrical stimulation module; and
a second power source, wherein the second power source provides power to at least the electrical stimulation module;
wherein the processor supplies power to the cardiac stimulation module from the second power source unless the second power source is depleted.

16. A method comprising:
delivering a cardiac stimulation therapy to a patient with a cardiac stimulation module of an implantable medical device (IMD) wherein the cardiac stimulation therapy selected from a group consisting of:
pacing;
cardioversion; and
defibrillation; and
delivering an electrical stimulation therapy to the patient with an electrical stimulation module of the IMD,
wherein the IMD includes a first power source which provides power to the cardiac stimulation module and not to the electrical stimulation module, and
wherein the IMD further includes a second power source, which provides power to at least the electrical stimulation module.

17. The method of claim 16, comprising employing batteries as the first and second power sources.

18. The method of claim 17, comprising employing a rechargeable battery as the second power source and recharging the rechargeable battery.

19. The method of claim 16, wherein the IMD further includes an inductive coil, the method further comprising transcutaneously charging the second power source via the inductive coil.

20. The method of claim 16, wherein the first power source comprises a first rechargeable battery, wherein the second power source comprises a second rechargeable battery, wherein the IMD further includes an inductive coil the method further comprising recharging the first and second batteries.

21. A method comprising:
delivering a cardiac stimulation therapy to a patient with a cardiac stimulation module of an implantable medical device (IMD) wherein the cardiac stimulation therapy selected from a group consisting of:
pacing;
cardioversion; and
defibrillation; and
delivering an electrical stimulation therapy to the patient with an electrical stimulation module of the IMD,
wherein the IMD includes a first power source which provides power to the cardiac stimulation module and not to the electrical stimulation module,
wherein the IMD further includes a second power source, which provides power to at least the electrical stimulation module; and
further comprising:
determining the second power source is depleted;
ceasing the electrical stimulation therapy after determining the second power source is depleted; and
continuing the cardiac stimulation therapy after determining the second power source is depleted.

22. The method of claim 21, further comprising:
charging the second power source; and
resuming the electrical stimulation therapy after charging the second power source.

23. A method comprising:
delivering a cardiac stimulation therapy to a patient with a cardiac stimulation module of an implantable medical device (IMD) wherein the cardiac stimulation therapy selected from a group consisting of:
pacing;
cardioversion; and
defibrillation; and
delivering an electrical stimulation therapy to the patient with an electrical stimulation module of the IMD,
wherein the IMD includes a first power source which provides power to the cardiac stimulation module and not to the electrical stimulation module,
wherein the IMD further includes a second power source, which provides power to at least the electrical stimulation module; and
wherein delivering electrical stimulation therapy comprises delivering neurostimulation.

* * * * *